United States Patent [19]

Bergersen

[11] Patent Number: 4,797,093
[45] Date of Patent: Jan. 10, 1989

[54] MUSCULAR EXPANSION BUMPER AND HEAD-GEAR APPLIANCE

[76] Inventor: Earl O. Bergersen, 950 Green Bay Rd., Winnetka, Ill. 60093

[21] Appl. No.: 109,938

[22] Filed: Oct. 19, 1987

[51] Int. Cl.$^4$ ................................................. A61C 7/00
[52] U.S. Cl. ............................................ 433/5; 433/7
[58] Field of Search ................................ 433/5, 6, 7

[56] References Cited

U.S. PATENT DOCUMENTS

| | | | |
|---|---|---|---|
| 4,272,241 | 6/1981 | Crisalli | 433/171 |
| 4,330,272 | 5/1982 | Bergersen | 433/5 |
| 4,637,796 | 1/1987 | Korn | 433/7 |

*Primary Examiner*—Robert Peshock
*Attorney, Agent, or Firm*—Hill, Van Santen, Steadman & Simpson

[57] ABSTRACT

A muscular expansion bumper appliance is optionally removable from a patient's mouth and includes a wire form member formed in a U-shape with the free ends which may be removably secured to buccal tubes. The wire form member supports at least one side pad which overlies one or both of the upper or lower posterior teeth to hold the user's cheeks away from those teeth to permit lateral posterior expansion. The side pads can be trimmed to custom fit the appliance to the user and the appliance comes in varying sizes.

15 Claims, 2 Drawing Sheets

FIG. 4

MUSCULAR EXPANSION BUMPER AND HEAD-GEAR APPLIANCE

BACKGROUND OF THE INVENTION

1. Field of the Invention

The present invention relates to orthodontic appliances and more particularly to an appliance for providing lateral expansion of the upper and/or lower posterior segments.

2. Description of the Prior Art

Frequently there is a lack of room for the front (especially lower) permanent incisors when they first erupt into the mouth at 7-9 years of age. This lack of room is frequently anteriorly across the front of the lower jaw because the permanent incisors are considerably larger than the deciduous teeth that preceeded them. If the lack of space is not corrected prior to the eruption of these permanent teeth, they rotate and are displaced out of position upon their eruption. The collagenous fibers then gradually form and hold them in their rotated and crowded position. If the teeth are eventually straightened, even with creation of additional space by whatever means, they frequently rotate back toward their original crowded and rotated positions. When similar teeth are straightened as they erupt at 7 or 8 years of age or shortly after, they tend to stay straight probably due to the collagenous fibers that are formed around these teeth after they were straightened. Since the erupting teeth were not allowed to become rotated and crowded and allowed to stay that way, the fibers were never formed originally in the rotated or crowded position. Therefore, it would be preferable to provide expansion at an early age, before the eruption of the lower permanent incisors at about from a very early age up to about 8 years of age as a form of preventive type orthodontic treatment. Or it can be done later or at any age when it seems appropriate to get expansion of the arches.

A drawback to expanding both the upper and lower posterior segments at the same time is that usually if one arch is expanded, the opposite arch must be expanded with another appliance which results in a mouth full of double appliance and is twice the appliance cost. A custom-made removable-type appliance known in the art as the "Frankel" has been used for expansion on the sides, but this requires that the user, generally a young child, keep the appliance in the mouth for a sufficient amount of time to provide the required effect. As can be expected, voluntary usage of such a device oftentimes leads to less than satisfactory results.

SUMMARY OF THE INVENTION

The present invention provides a single device which can be preformed and can be a fixed type of appliance utilized on a bumper, therefore being removable only by a dentist or also by the patient if required or in an emergency. The entire appliance can be preformed or can be supplied as a metal form to be custom-made to add side pads or front pads as needed, used for the expansion as a custom-fit to a model of the mouth. The bumper embodying the principles of the present invention is used to provide lateral expansion of the upper posterior segments or the lower posterior segments or both at the same time through the use of a single appliance or expansion in the front section by increasing the pad size in front. If expansion is required across the upper front, the appliance is made to fit into upper molar bands the same way that it fits in the lower. The expansion bumper can be designed to fit into buccal tubes on the first or second permanent molars or to the second deciduous molars on either the upper or lower arch.

The appliance is designed on the side of the posterior region to hold a plastic shield that can be molded around the wire support. The wire support can take various shapes as an all in one bent wire or a soldered addition. The added soft pliable plastic will allow the pads to be adapted to the mouth to avoid soft-tissue impingement by bending the inside wire and the plastic will deform along with the wire. Or the plastic can be of the type that is either hard or pliable at the mouth temperature but can be remoldable with an increase in the temperature or can be of a self curing acrylic or any other moldable plastic or rubber silicon material or pliable or hard moldable material.

This appliance can be made in various sizes to fit various sized mouths, that is for example small, medium and large or as many as necessary to enable the appliance to function in the mouth when chewing, etc., without getting sore spots or being uncomfortable. It can also be made for the deciduous dentition, mixed dentition or adult dentition.

The present appliance provides advantages over devices previously utilized in its ability to expand the posterior segments in a lateral direction as it is driving the molars distally and can also move the front teeth forward all at the same time while being used in the mouth. Also, since it is able to expand both the upper and lower posterior segments at the same time with a single appliance, drawbacks of having excessive numbers or amounts of appliances in the mouth is avoided. As mentioned, the appliance can be fixed within the mouth by attachment to the buccal tubes or can be utilized with a head gear to provide additional distal drive to the molars, or added to any form of head-gear device when not actually secured to the posterior teeth.

BRIEF DESCRIPTION OF THE DRAWINGS

FIG. 4 is a sectional view taken generally along the line IV—IV of FIG. 3.

DESCRIPTION OF THE PREFERRED EMBODIMENTS

Figure 6:
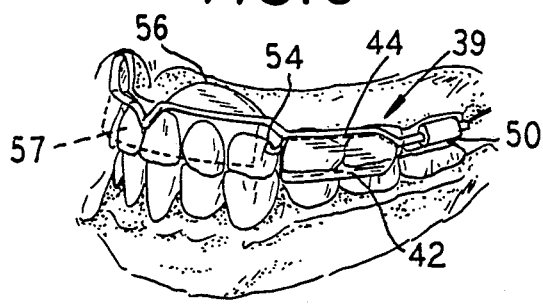
FIG. 6 is a perspective view of an expansion bumper incorporating the principles of the present invention attached to the upper arch.
Figure 7:
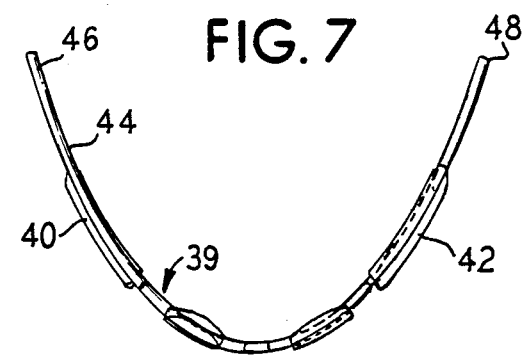
FIG. 7 is a top view of the bumper of FIG. 6 shown alone.
Figure 8:
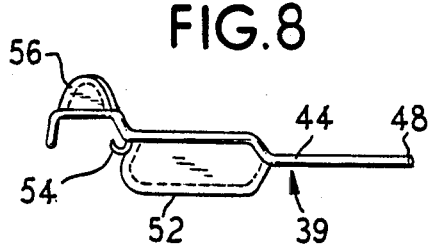
FIG. 8 is a buccal view of the expansion bumper of FIG. 7.
Figure 9:
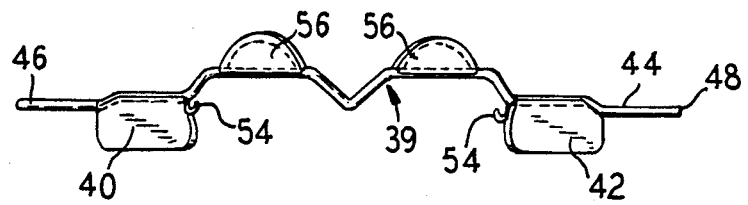
FIG. 9 is an anterior view of the bumper of FIG. 7.

The present invention provides a bumper where individual lateral expansion of the upper posterior segments (FIGS. 6–9), or of the lower posterior segments (FIGS. 10–11), or of both at the same time (FIGS. 1–5 and 12–13) can be performed, or of the anterior segment of upper (FIG. 6 in phantom) or lower (FIGS. 1 and 3 in phantom) as well.

Figure 1:
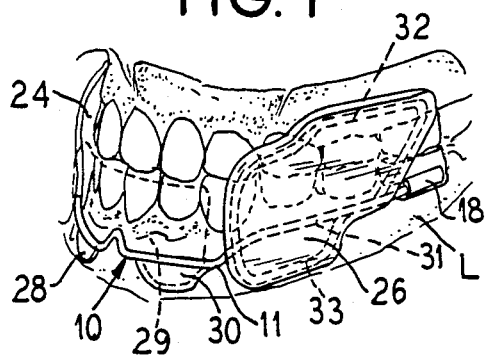
FIG. 1 is a perspective view of an expansion bumper incorporating the principles of the present invention.
Figure 2:
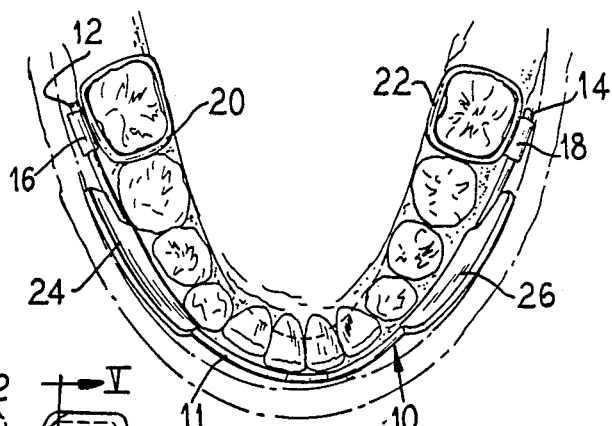
FIG. 2 is an occlusal view of the lower arch illustrating the expansion bumper of FIG. 1.

In FIGS. 1–5 there is illustrated a muscular expansion bumper generally at 10 which, although secured to a lower arch L, can be used to provide expansion of both the upper posterior segment as well as the lower posterior segment. The bumper is formed in a generally U-shaped configuration as seen in FIG. 2 with a wire form member 11. Free ends 12, 14 of the U-shaped configuration being a single projecting wire, each of which is to be received in a buccal tube 16, 18 secured to a molar band 20, 22 held on the first permanent molar as illustrated in FIG. 2. The band can also be attached to the second permanent molar or second deciduous molar depending on the patient's stage of dentition, or any other tooth or instead of a band, the tube can be directly bonded to the enamel of the tooth without having a band around the tooth.

The bumper includes two lateral side pads 24, 26 formed from a resilient plastic material which extend superiorly and inferiorly of the wire form member 11 from a posterior position close to the free end of the U-shaped frame that is secured in the buccal tubes to an anterior position so as to overlie the buccal sides of the molars, premolars or bicuspids, and canines.

The wire form member 11, which is attached solely at its free ends 12, 14 to the molars, is spaced away from the teeth which it overlies to remove the buccal and labial pressure normally applied to the teeth so as to permit lateral expansion, particularly in the posterior segment from the action of the tongue. The band also includes anterior pads 28, 30 to hold the lower lip away from the lower incisors to permit expansion in that area and to provide distal pressure on the anchoring molar. These front pads 28, 30 can be positioned low only for anchorage or high as illustrated in phantom at 29 for labial tooth movement, or both high and low for both functions.

The wire form member 11 is shown in FIGS. 1–5 as being comprised of a single continuous wire 31 having the general U-shape with added wire segments extending superiorly 32 and inferiorly 33 of the continuous wire 31 to provide an increased area support for the pads. The pads themselves are molded onto the wire form and wire segments and are contoured in a vertical direction such that they curve in a buccal direction from the continuous wire form portion to hold the cheeks sufficiently away from the teeth so as to permit the desired expansion. The use of the wire segments permits an add on of side pads of various dimensions to extend or diminish the function or effect of these pads on the wire. The extensions can be in separate pieces so to be soldered in place by a custom finisher, or can be in one wire configuration for easier molding. In a lab or dentist hand-made adaptation setting, the shield could be acrylic (self cure or cureable) instead of injection molded. Also, the pads extend outwardly beyond the added wire segments 32, 33 to form a peripheral margin area which may be selectively trimmed by the dentist to provide a custom fit of the pads.

FIGS. 6–9 illustrate an appliance 39, similar to that illustrated in FIGS. 1–5, but the appliance in FIGS. 6–9 is attached to the upper molars and includes side pads 40, 42 to overlie only the upper bicuspids to provide lateral expansion of only the upper posterior segments. Again, the appliance is comprised of a continuous U-shaped wire form member 44 having free posterior ends 46, 48 which are received in buccal tubes 50 secured to the upper molars. A wire addition 52 is soldered to the wire form member 44 to provide an increased support shape for the side pads 40, 42. As is common in appliances used in the mouth, hooks 54 for receiving elastic bands may also be attached to the wire frame 44. Upper labial pads 56 are also provided on the appliance of FIGS. 6–9 to hold the upper lip away from the upper incisors and to provide distal pressure to the anchoring molars.

Figure 10:
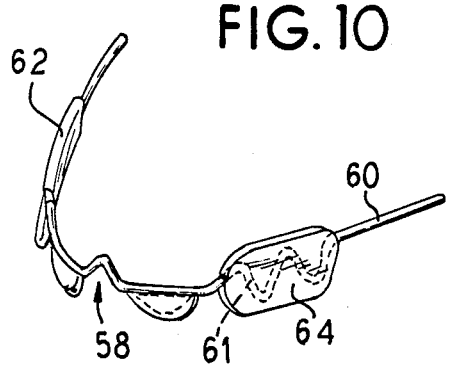
FIG. 10 is a perspective view of an expansion bumper incorporating the principles of the present invention having a differing interior wire form.
Figure 11:
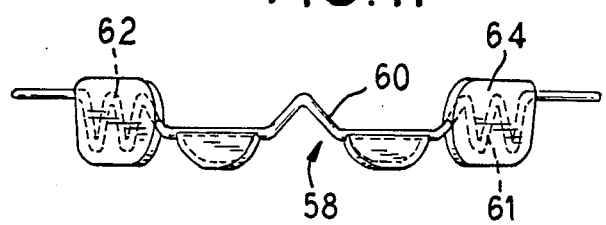
FIG. 11 is an anterior view of the bumper of FIG. 10.

FIGS. 10 and 11 illustrate an appliance 58 which can be used for providing lateral expansion of only the lower posterior segment in which a single continuous wire form member 60 is formed in a U-shape as seen from above and which includes a serpentine configuration 61 or W-shape in the region where buccal side pads 62, 64 are molded on the wire form member 60. In all other respects, the form of the appliance 58 is substantially similar to appliance 39 of FIGS. 6–9, except of course that appliance 58 is to be used for lower lateral expansion and appliance 39 is to be used for upper lateral expansion.

Figure 3:
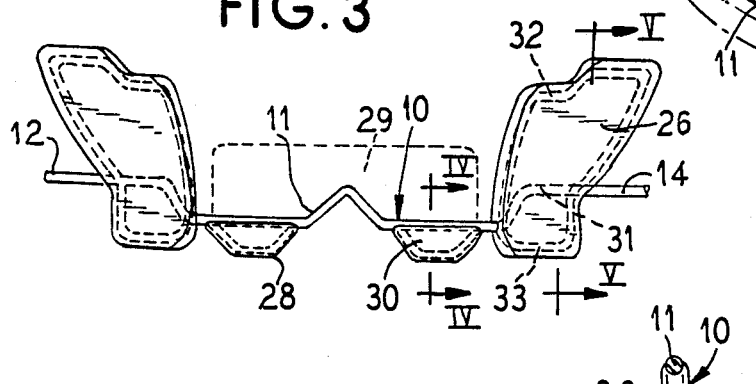
FIG. 3 is an anterior view of the expansion bumper of FIG. 1 alone.
Figure 5:
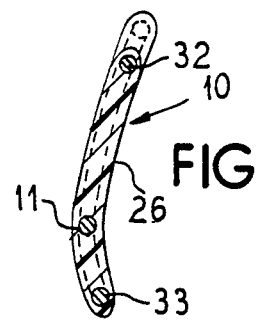
FIG. 5 is a sectional view taken generally along the line V—V of FIG. 3.
Figure 12:
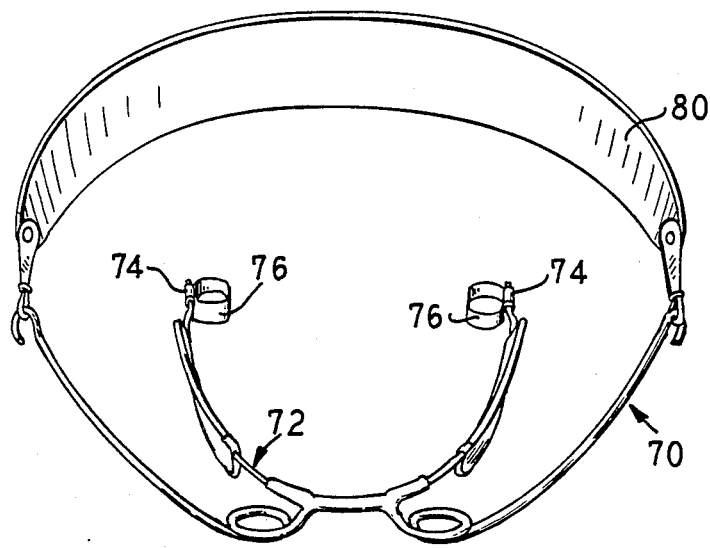
FIG. 12 is a top perspective view of an expansion bumper incorporating the principles of the present invention and utilized with a head gear.
Figure 13:
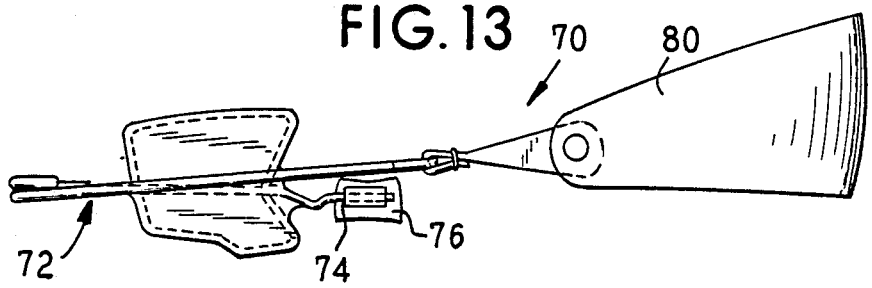
FIG. 13 is a buccal elevational view of the head gear appliance of FIG. 12.

FIGS. 12 and 13 illustrate a head gear appliance 70 which includes a muscular expansion bumper 72 incorporating the principles of the present invention as described above. The expansion bumper 72 is substantially identical to the embodiment illustrated in FIGS. 1–5 in that it is used for lateral expansion of the upper posterior segments and lower posterior segments at the same time and is secured to buccal tubes 74 on molar bands 76 positioned on the upper or lower molars. Since the head gear appliance includes a strap 80 which encircles the user's head to provide the distal drive to the molars, the anterior labial pads illustrated in FIGS. 1–3 are not required but can be used if labial movement of upper incisors is required or alveolar bone apposition is needed or if additional distal movement of molars is desired.

Thus, it is seen that the present invention provides an appliance which effects lateral expansion of the upper and lower posterior segments alone or at the same time, the appliance being fixed within the user's mouth so that treatment is not dependent upon voluntary participation by the user which generally is a child, thereby increasing the effectiveness of the appliance. In some applications it could be removable from the bands. Further, the appliance provides the expansion, and particularly combined upper and lower expansion with a minimal amount of hardware to be placed in the user's mouth. It can also provide anterior expansion as well with pads placed at varying levels in the front of the mouth.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A muscular expansion bumper appliance comprising:
   a wire form member having a generally U-shaped configuration having a central bight portion with two free posterior ends,
   at least one additional wire segment secured on a lateral side of at least one of said free posterior ends of said wire form member, said wire segment configured into a generally geometrical parallelogram shape, and
   a side pad comprising a moldable material molded onto and carried by said wire segment and together with said wire segment forming a selectively deformed side pad to permit desired expansion.

2. A muscular expansion bumper appliance according to claim 1, wherein said side pad extend beyond said wire segment to permit portions of said pad to be trimmed to custom fit the appliance to the user.

3. A muscular expansion bumper appliance for use in correcting human dentition comprising:
   a wire form member having a generally U-shaped configuration having a central bight portion with two free posterior ends;
   at least one side pad secured to said wire form member and extending vertically at least one of superior to or inferior to said wire form member;
   said side pad positioned on said wire form member between said free ends and said central bight portion, and
   said wire form member having a serpentine configuration on at least one lateral side and said side pad being molded onto at least one side and being molded onto said serpentine portion to prevent rotation of said pad on said wire form member.

4. A muscular expansion bumper appliance according to claim 3, wherein there are a plurality of side pads which extend both superior to and inferior to said wire form member.

5. A muscular expansion bumper appliance according to claim 3, wherein said side pad is formed from a moldable material.

6. A muscular expansion bumper appliance according to claim 3, wherein one side pad is provided on each lateral side of said wire form member.

7. A muscular expansion bumper appliance according to claim 3, wherein said wire form member attaches to a strap to form a part of a head gear appliance.

8. A muscular expansion bumper appliance for use in providing posterior lateral expansion of human dentition comprising:
   a wire form member having a generally U-shaped configuration with two free posterior ends, said ends being removably secured in buccal tubes for attachment a user's molars;
   at least one side pad secured to said wire form member to overlie the buccal side of at least one of the upper or lower posterior teeth of the user,
   whereby, the user's cheeks will be held away from the adjoining teeth to permit posterior lateral expansion to occur.

9. A muscular expansion bumper appliance according to claim 8, wherein said side pads overlie both upper and lower teeth.

10. A muscular expansion bumper appliance according to claim 8, wherein said side pads are formed from a moldable material.

11. A muscular expansion bumper appliance according to claim 8, wherein said form member attaches to a strap to form a part of a head gear appliance.

12. A muscular expansion bumper appliance according to claim 8, wherein an additional wire segment is secured on at least one lateral side of said wire form member and said side pad is molded onto said wire segment.

13. A muscular expansion bumper appliance according to claim 12, wherein said side pad extends beyond said wire segment to permit portions of said pad to be trimmed to custom fit the appliance to the user.

14. A muscular expansion bumper appliance according to claim 8, wherein said wire form member has a serpentine configuration at least one lateral side and said side pad is molded onto said serpentine portion.

15. A muscular expansion bumper appliance according to claim 8, wherein said side pads are formed from a heat sensitive bendable plastic at higher than mouth temperature.

* * * * *